United States Patent [19]

Kalo

[11] Patent Number: 5,493,055
[45] Date of Patent: Feb. 20, 1996

[54] PROCESS FOR THE MANUFACTURE OF P-PHENETIDINE

[75] Inventor: Jacob Kalo, Akko, Israel

[73] Assignee: Tambour, Ltd., Akko, Israel

[21] Appl. No.: 418,078

[22] Filed: Apr. 6, 1995

[30] Foreign Application Priority Data

May 6, 1994 [IL] Israel ......................................... 109576

[51] Int. Cl.$^6$ ................................................. C07C 209/42
[52] U.S. Cl. .......................... 564/415; 534/588; 534/596; 564/443
[58] Field of Search ..................... 564/415, 443

[56] References Cited

U.S. PATENT DOCUMENTS

| | | | |
|---|---|---|---|
| 2,571,091 | 10/1951 | Wasserman | 260/575 |
| 4,124,640 | 11/1978 | Shinohara et al. | 260/575 |
| 5,382,691 | 1/1995 | Stern et al. | 564/415 |

FOREIGN PATENT DOCUMENTS

| | | |
|---|---|---|
| 146650 | 12/1972 | Czechoslovakia . |
| 2649741 | 9/1977 | Germany . |
| 53-84925 | 6/1977 | Japan . |
| 514811 | 9/1976 | U.S.S.R. . |

*Primary Examiner*—Shailendra Kumar
*Assistant Examiner*—Brian M. Burn
*Attorney, Agent, or Firm*—Morgan & Finnegan

[57] ABSTRACT

A process for the manufacture of para-phenetidine is described. The process comprises the following steps: (a) diazotizing para-phenetidine and coupling the resulting compound to phenol at a molar ratio of 1.3 to 1 phenol to the diazo compound;(b) ethylating the resulting compound at a temperature in the range of between 130° C. to 200° C., and (c) catalytically hydrogenating the ethylated compound, whereby two moles of para-phenetidine are produced, one of which being recycled as the starting reagent in the first step. The product obtained is of a high purity being substantially free from the undesired isomers.

10 Claims, No Drawings

PROCESS FOR THE MANUFACTURE OF P-PHENETIDINE

The present invention relates to a novel process for the manufacture of p-phenetidine. More particularly, the invention relates to an improved process for the manufacture of p-phenetidine of a high purity without co-producing large quantities of by-products.

BACKGROUND OF THE INVENTION p-phenetidine is an important compound used as intermediate in the dyes industry as well as for many other uses. Thus for instance, it is used in the manufacture of p-ethoxyacetanilide and Ethoxyquin. Due to the large amounts of p-phenetidine required, there are many patents and publications which describe different methods, the aim in all of which being to improve the yield and purity of the product, thus reducing its cost.

The general scheme for the manufacture of p-phenetidine includes three main steps:

(a) Nitration of chlorobenzene by a mixture of sulfuric acid and nitric acid. The product obtained is a mixture of 70% p-chloro nitrobenzene and 30% o-chloro nitrobenzene. The o-nitro chlorobenzene obtained as a by-product, has to be recovered.

(b) Ethoxylation of the p-chloro nitrobenzene using a base and ethyl alcohol in the presence of a catalyst. The reaction is conducted for several hours, the chlorine being replaced by the ethoxy group. Yields in the range of 80% to 90% are mentioned to be obtained.

(c) Catalytic reduction of the nitro group at about 100° C. under pressure in the presence of a catalyst selected from nickel or a noble metal. This reduction is carried out in the presence of a solvent which at the end of the reaction should be evaporated and the p-phenetidine is distilled out under vacuum.

Several improvements were suggested to the above scheme, all claiming that they improve the overall yield or costs of the final product. Some typical examples of a number of prior patents will be hereinafter described.

According to German Offen. 2,649,741, alkoxyanilines are prepared by treating the corresponding aniline with RX, wherein X is Cl or Br, in an aprotic organic solvent in the presence of an alkali metal alcoholate or hydroxide. The reaction is carried out in an autoclave at 80° C. for 5 hours obtaining the alkoxyaniline at an yield of 89.5%.

According to Russian Patent Number 514,811, p-phenetidine is obtained by the reduction of p-nitrophenol in absolute alcohol in the presence of concentrated sulfuric acid, using platinum oxide as a catalyst and dimethyl sulfoxide as a promoter. The product is finally obtained by heating the mixture under a nitrogen medium.

According to Japanese Kokai 53/84925 (78/84925) alkoxy-anilines anilines are prepared by the reduction of p-nitrophenol with hydrogen dissolved in an alcohol in the presence of: organo-sulfonic acids or alkyl esters of sulfuric acid, platinum or paladium and sulfuric acid. The reaction is carried out under pressure for about seven hours at 70–80 degrees C., yielding 69% of p-alkoxyaniline.

According to Roumanian Patent Number 54273, p-phenetidine is obtained by the reduction of p-nitrophenetole with iron in an aqueous solution of ammonium chloride using a permanent excess of iron in the reaction medium exempt of free acidity. The precipitate of $Fe_3O_4$ obtained was filtered under pressure and washed by steam. The filtrate was further treated with sodium chloride yielding the p-phenetidine.

An interesting process is described in the Czech Patent Number 146650 starting with phenol. In a first step the phenol is coupled with diazotized aniline and subsequently ethylated with ethyl chloride. The resulted product was cleaved at 30°–60° C. under pressure of hydrogen over a palladium on carbon catalyst. The yield claimed to be obtained is only about 90%.

The above brief review illustrates the importance attributed to the manufacture of p-phenetidine the aim being to improve some of the stages involved in the process, in order to increase the yield or purity of the final product.

It is an object of the present invention to provide a simple process for the manufacture of p-phenetidine. It is another object of the present invention to provide a simple process for the manufacture of p-phenetidine at high yields. It is yet another object of the present invention to provide a simple process for the manufacture of p-phenetidine which is substantially free of the undesired isomers o-phenetidine and chloro-amino aromatics.

BRIEF DESCRIPTION OF THE INVENTION

The invention consists of an improved process for the manufacture of p-phenetidine which comprises the steps of: (a) diazotizing p-phenetidine and coupling the resulting compound to phenol at a molar ratio of 1.3–1.0 phenol to diazo; (b) ethylating the compound obtained in step (a) at a temperature in the range of between 130°–200 C. and (c) catalytically hydrogenating the ethylated compound obtained in step (b) whereby 2 moles of p-phenetidine are produced, one of which being recycled as starting reagent in step (a). It was found that under specific critical conditions yields of above 97% are achieved. Moreover, since the main starting reagent consists of one mole of the final product which was obtained in the process, the purity of the final p-phenetidine may be selected according to the intended specific use. Thus, starting with a very pure p-phenetidine, on which the diazotizing coupling is carried out, a corresponding very pure product will result.

The first step is very critical and determines the yield of the p-phenetidine which is achieved. In this step, two consequent reactions are involved: the first reaction, in which the diazonium salt is obtained using a nitrite salt, such as sodium nitrite, in acidic conditions under cooling below 10° C., the preferred temperature being in the range of between 0° C. to 5° C. In the subsequent reaction, the diazonium salt is coupled with phenol, in an alkaline medium maintaining a slight excess of diazo to phenol, the most preferred molar ratio being 1.0 to 1.3. The reactions involved are schematically as follows:

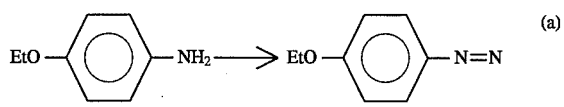

(a)

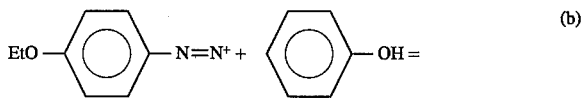

(b)

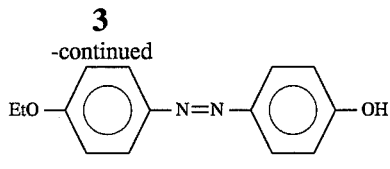

It was surprisingly found that the slight excess of phenol to diazo is very critical to the yield which can be achieved. Although the reaction is feasible even in an excess of 2 moles phenol to diazo, it was found that then a decrease in the yield will occur. The acidic conditions required for the first reaction are obtained by using any mineral acid, such as hydrochloric or sulfuric acid. The coupling reaction with the phenol is carried out in a basic medium, the pH being in the range of between 9 to 10 and most preferably in the range of between 9.2 to 9.4. The basic medium may be obtained by the use of any alkaline compound such as sodium hydroxide, sodium carbonate, sodium bicarbonate, potassium hydroxide, the first one being the most preferred from an economical point of view.

The second stage involves the ethylation of the coupled compound obtained in the first step, using an ethyl halide or ethyl sulfate in the presence of a solvent and a basic substance at a temperature in the range of 130° C. 200° C. Generally, an excess of the coupled compound should be present, preferably the molar ratio being at least 1.3 moles of the ethylating compound to 1 mole of the coupled compound. The solvent to be used should be inert towards the components of the reaction and may be selected from a broad class such as acetonitrile, xylenes, methanol, ethanol, toluenes, etc. The equation which illustrates the second step, can be schematically presented as follows:

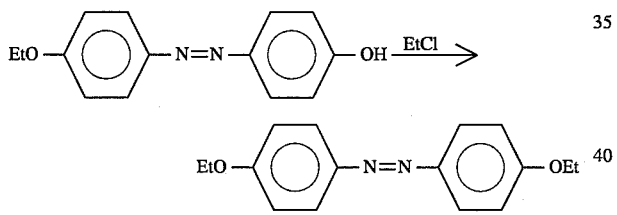

The last step, involves the catalytic reduction of the ethylated coupled compound and is very critical for obtaining the high yield according to the present invention. In the reaction which takes place, the azo bond (N=N) is cracked and in the presence of hydrogen, two moles of amine compound, i.e p-alkoxyaniline, are produced. It was found that this reaction should be carried out at a temperature above 70° C. under a pressure of above 5 atmospheres of hydrogen in the presence of an inert solvent and a catalyst selected from nickel or a noble metal such as palladium, platinum, iridium, etc. on an inert support. The inert solvent may be selected from various commercial alcohols. It is also possible to carry out the reduction reaction in the absence of said alcohol in which case the temperature should be in the range of 40° C.–160° C.

The equation involved for the second stage can be schematically presented as follows:

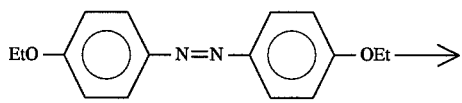

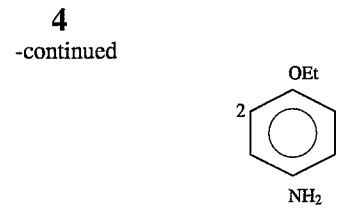

As appears from the above equation, 2 moles of the desired product are obtained, one being recycled in the first stage in the reaction of diazotizing. Therefore, the process according to the present invention does require only common starting reagents such as phenol, ethyl chloride, mineral acid and basic reagents to obtain valuable final products of a high purity and high yields.

The invention will be hereafter illustrated by the following Examples without being limited thereto. A person skilled in the art after reading the present specification, will be in a position to appreciate the gist of the invention and many variations might be conceived and incorporated as encompassed by the appended claims.

EXAMPLE 1

Step a: Preparation of 4-Etoxy-4'-hydroxy-azobenzene.

In a 5 liter plastic vessel equipped with a stirrer, there were added: 1 liter water, 0.5 kg crushed ice, 145 g concentrated sulfuric acid (98%) and 137.2 g of distilled p-Phenetidine (obtained from a previous cycle). The reaction mixture was kept at about 0° C. by the addition of more crushed ice and then 230 g of 33.3% $NaNO_2$ solution was introduced rapidly under the surface.

The reaction involved was as follows:

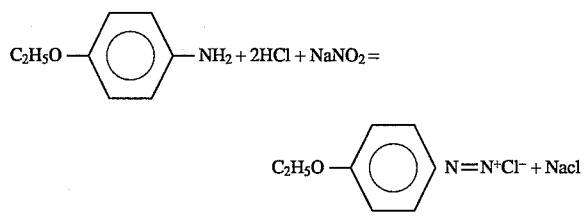

This diazo solution was stirred for 1 hr, while the temperature was kept around 0° C.

The product obtained was subsequently coupled with phenol as follows:

Into a 10 liter vessel, equipped with a stirrer, there were added:

1 liter $H_2O$, 97 g phenol and a solution of sodium hydroxide, thus rising the pH to 9.3. Then, the diazo solution, obtained in step (a) above, was added under the surface during approximately 1 hr, while the pH value was kept between 9.2–9.5, by the addition of a solution of 10% sodium hydroxide. The reaction mixture was stirred for an additional period of 30 minutes, and then the pH was adjusted to 6.5–7.5 by a diluted solution of sulfuric acid. The reaction involved was as follows:

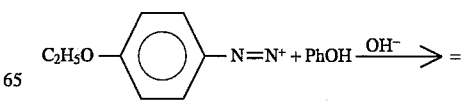

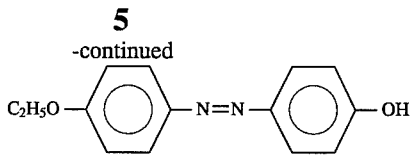

The product was filtered, washed with water until the cake was free of salts and dried at 45° C.–50° C.

An amount of 236 grams of 4-etoxy-4'-hydroxy-azobenzene, was obtained i.e.: a yield of 97.5% of the theoretical one. The m.p. of the product was 126° C.–128° C.

Step b: Preparation of 4,4'-dietoxy-azobenzene.

Into a pressure vessel equipped with a stirrer, the reagents were introduced in the following order:

(a) 150 ml methanol;

(b) 36.6 g concentrated sodium hydroxide (46.5% by wt.);

(c) 98.5 g dry 4-etoxy-4'-hydroxy-azobenzene.

(d) 10.0 g anhydrous sodium carbonate.

The reactor was cooled to about 15° C. and then 33.6 g of ethyl chloride were added.

The reactor was heated to 160° C. while a vigorous agitation was maintained. After 1 hr. the reactor was cooled, the product was filtered and washed with a dilute solution of sodium hydroxide, then with a dilute solution of sulfuric acid followed by water until a pH in the range of between 6.0 to 8.0 was obtained in the rinse water. The product was then dried at 120° C.

An amount of 108.0 grams of 4,4'-dietoxy-azobenzene was obtained, i.e. 98.3% yield of the theoretical. Its melting point was 160° C.–161° C.

Step 3

Catalytic Hydrogenation of 4,4'-dietoxy-azobenzene.

Into a 0.4 liter pressure vessel, equipped with a thermometer and a mechanical stirrer there were introduced the following reagents:

(a) 200 ml methanol;

(b) 0.20 g of a catalyst, consisting of 5% Pd on carbon, in the form of a paste containing about 50% water.

(c) 20.0 g 4,4'-dietoxy-azobenzene.

The reactor was closed, flushed 3 times with nitrogen and once with hydrogen at ambient temperature. Then hydrogen was introduced to give a pressure of 8 atm. at ambient temperature. The reactor was then heated to 100° C. while maintaining a continuous feed of hydrogen and a vigorous stirring.

After 30 min the reaction was completed and the reaction mixture cooled and filtered. The solvent was evaporated and the crude p-phenetidine was distilled under vacuum.

An amount of 19.7 gr of product was obtained, i.e. 97% yield of the theoretical having a refractive index of $N^{20}d=1.0650$.

EXAMPLE 2

The experiment as in Example 1 was repeated, wherein the steps (a) and (b) were the same, using the same reagents and amounts.

In step (c), the hydrogenation was carried out as in Example 1, in the same pressure vessel starting with the p-phenetidine obtained in Example 1, the other reagents and amounts in step (a) and (b) being the same, but the catalyst used in step (c) consisted of 1.0 g of Raney Nickel (60% solids).

Also in this case the same amount of 19.7 of p-phenetidine product was obtained having the same refractive index of $N^{20}d=1.0650$.

While the invention has been described in connection with certain preferred embodiments, it will be understood that it is not intended to limit the invention to those particular Examples. On the contrary, modifications beyond the particular Examples, as may be included within the scope of the invention, should be considered to be covered by the present patent application. It should be understood that the particulars described are by way of example without being limited thereto.

I claim:

1. A process for the manufacture of p-phenetidine which comprises the steps of:

(a) diazotizing p-phenetidine and coupling the resulting compound to phenol at a molar ratio of 1.3–1.0 phenol to diazo;

(b) ethylating the compound obtained in step (a) at a temperature in the range of between 130° C.–200° C.; and (c) catalytically hydrogenating the ethylated compound obtained in step (b) whereby 2 moles of p-phenetidine are produced, one of which is recycled as starting reagent in step (a).

2. The process for the manufacture of p-phenetidine according to claim 1, wherein the diazotizing reaction is carried out at a temperature in the range of between 0° C. to 5° C.

3. The process for the manufacture of p-phenetidine according to claim 1, wherein the coupling of the diazotizing compound to phenol, is carried out at a pH in the range of between 9 and 10.

4. The process according to claim 3, wherein said pH is maintained by adding a basic compound selected from the group consisting of sodium hydroxide, sodium carbonate, sodium bicarbonate and potassium hydroxide.

5. The process according to claim 1, wherein said ethylation reaction is carried out with a reagent selected from the group consisting of ethyl chloride and ethyl sulfate, in the presence of an inert solvent.

6. The process according to claim 5, wherein the molar ratio between the coupled compound to the ethylating reagent is in the range of between 1.0 to 1.3.

7. The process according to claim 5, wherein said ethylation is carried out at a temperature in the range of between 130° C. to 200° C.

8. The process according to claim 5, wherein said inert solvent is selected from the group, consisting of xylene, toluene, methanol, ethanol and acetonitrile.

9. The process according to claim 1, wherein the catalytic hydrogenation of the ethylated compound is carried out at a temperature above 70° C. under a pressure of 5 atmospheres of hydrogen in the presence of an inert solvent and a catalyst.

10. The process according to claim 9, wherein said solvent is an inert alcohol.

* * * * *